United States Patent [19]

Cunningham et al.

[11] Patent Number: 4,522,196

[45] Date of Patent: Jun. 11, 1985

[54] REUSABLE, STERILE COVERING FOR A SURGICAL CAMERA

[76] Inventors: Frank W. Cunningham, 1801 Via Estudillo, Palos Verdes Estates, Calif. 90274; David Weir, 1602 Royce St., Camarillo, Calif. 93010

[21] Appl. No.: 619,683

[22] Filed: Jun. 11, 1984

Related U.S. Application Data

[63] Continuation of Ser. No. 387,353, Jun. 11, 1982, abandoned.

[51] Int. Cl.$^3$ ................................................ A61B 1/00
[52] U.S. Cl. ...................................... 128/4; 350/587; 354/62
[58] Field of Search ............................. 128/1 R, 4–8, 128/132 D; 350/319, 579, 582, 587, 585, 589, 61; 150/52 J, DIG. 1; 354/62

[56] References Cited

U.S. PATENT DOCUMENTS

| | | | |
|---|---|---|---|
| 1,535,312 | 4/1925 | Hosking | 150/525 |
| 3,528,720 | 9/1970 | Treace | 350/61 |
| 3,900,021 | 8/1975 | Makepeace et al. | 128/4 |
| 4,318,395 | 3/1982 | Tawara | 128/4 |

FOREIGN PATENT DOCUMENTS 821235 10/1959 United Kingdom ................ 350/589

Primary Examiner—Edward M. Coven
Assistant Examiner—Max F. Hindenburg
Attorney, Agent, or Firm—Fulwider, Patton, Rieber, Lee & Utecht

[57] ABSTRACT

A sterile covering enabling an endoscope to be attached to or detached from a camera coupling without contamination by either the camera or the coupling. The sterile covering encloses the camera and is disposed within a cavity of a C-mount coupling which couples the endoscope to the camera. The covering includes a system for registering an optically clear portion of the covering, an optically clear film, or an element coupled to the covering with the endoscope-to-camera optical path. In one embodiment, the same system which establishes optical registration also enables attachment of the covering to the C-mount coupling, thereby providing an optically clear, fluid-impermeable barrier between the endoscope and the camera, and eliminating possible contamination of the endoscope by either the C-mount coupling or the camera.

8 Claims, 8 Drawing Figures

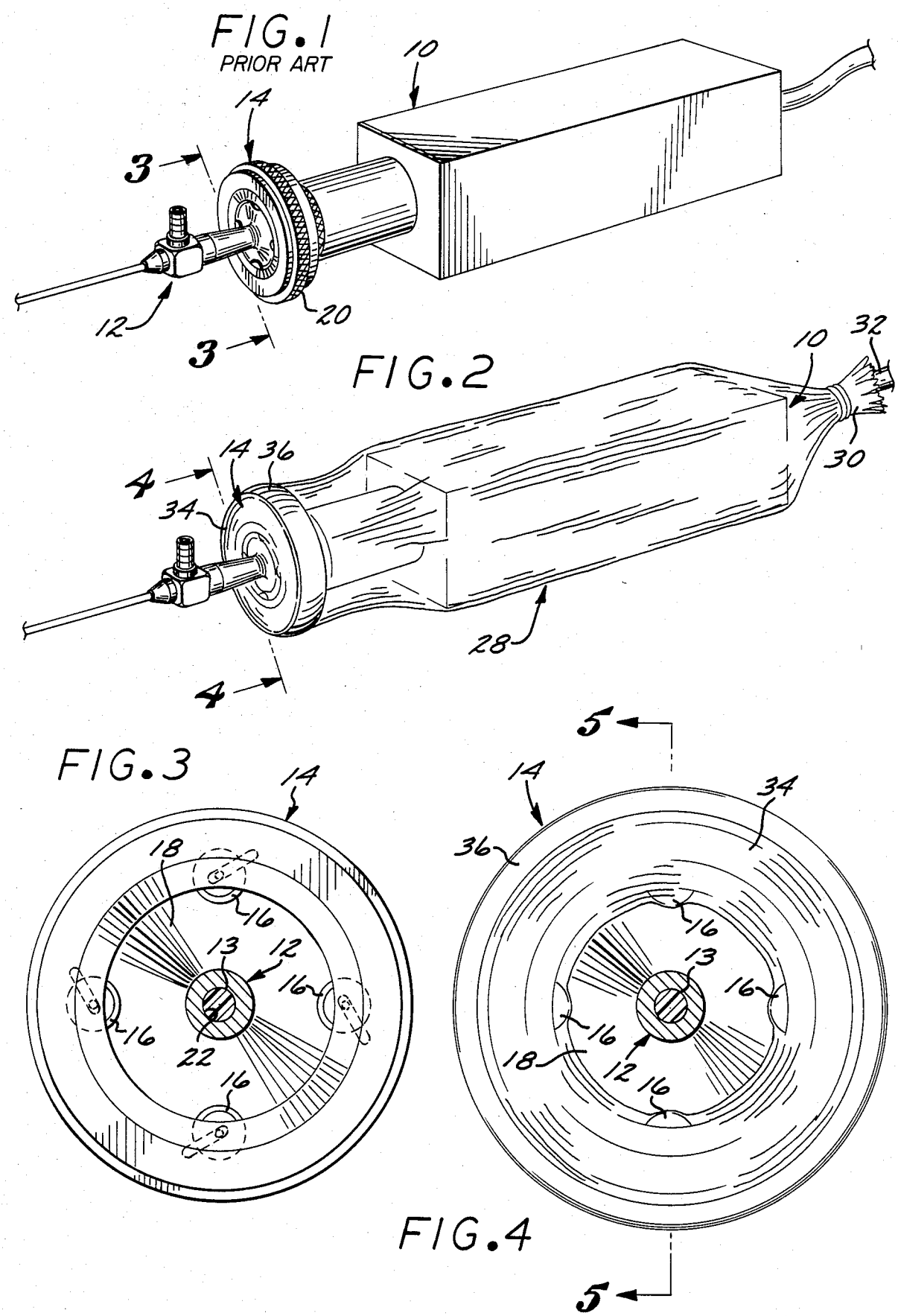

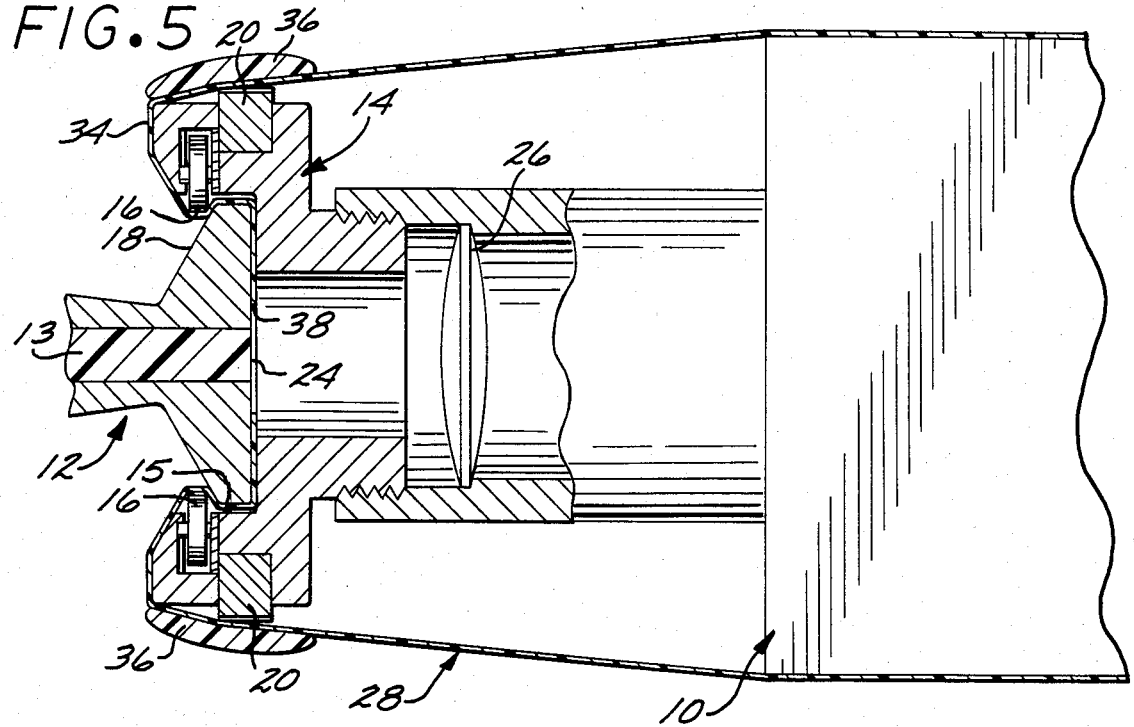
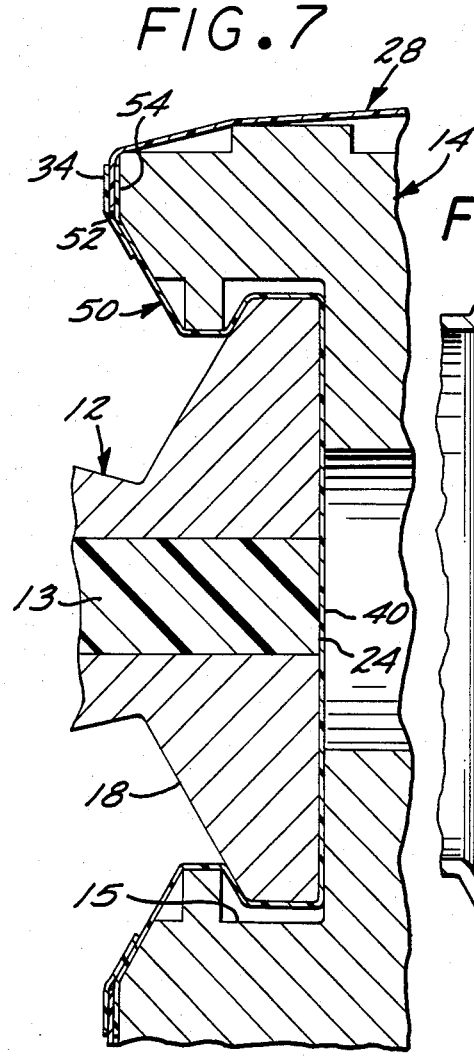
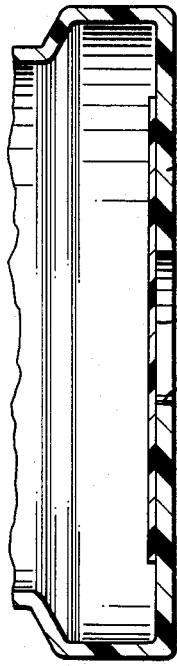
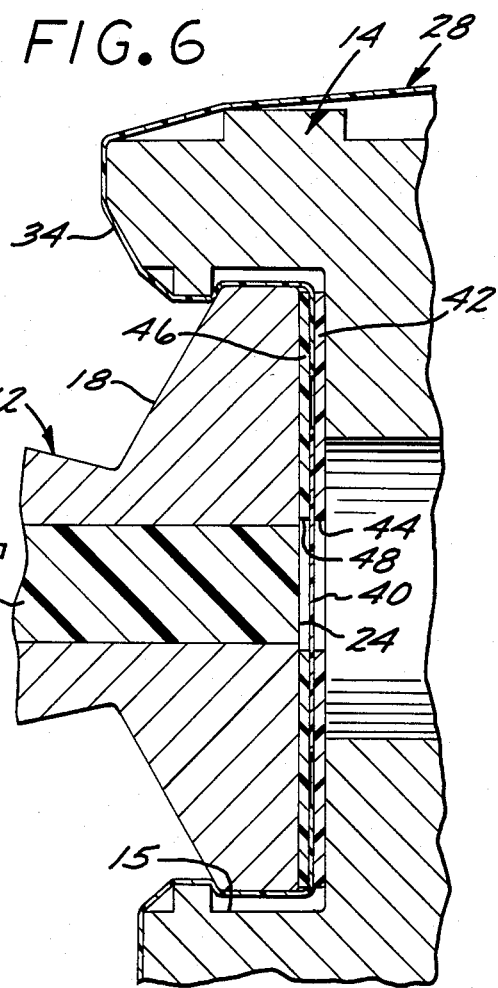

REUSABLE, STERILE COVERING FOR A SURGICAL CAMERA

This is a continuation, of application Ser. No. 387,353, filed June 11, 1982 now abandoned.

BACKGROUND OF THE INVENTION

1. Field of the Invention

The present invention relates to biomedical apparatus, and particularly to a sterile covering for a surgical camera used in arthroscopic operations.

2. Description of the Prior Art

Arthroscopy involves the use of filamentary probes, such as an endoscope, which is a filamentary tube particularly adapted for transmitting an optical image of a remote surgical site. The image can be seen through the endoscope with the naked eye, but it is more typically picked up by a television camera and enlarged for display on a video screen. A typical coupling between an endoscope and a camera is shown by Makepeace, et al., U.S. Pat. No. 3,900,021.

Although endoscopes are designed to be autoclaved for sterilization, it is impractical sterilize a television camera and its coupling. Therefore, once an endoscope has been connected to the coupling, that portion of the endoscope coming into contact with the coupling is regarded as contaminated according to surgical practice. The contaminated endoscope must then be resterilized before reuse, or a separate, sterilized endoscope used in its place.

In prior art practice, a sterile plastic covering or bag is placed over the camera to form a sterile barrier between the camera and the operating environment. Typically, the bag is tied off tightly around that end of the endoscope nearest the camera.

Several endoscopes are typically used during an operation, each endoscope having a different shape or characteristic. Each time an endoscope is attached or detached from the camera coupling, the end of the sterile bag must be untied and retied to uncover and recover the endoscope-to-camera coupling. However, as discussed above, once an endoscope is decoupled from the camera, it is treated as contaminated and cannot be reused unless resterilized.

What is needed is some means for providing a sterile covering for a camera which allows a succession of endoscopes to be attached and detached from the camera coupling without contamination from the camera or its coupling, and without destroying the sterility of the camera covering.

BRIEF SUMMARY OF THE INVENTION

The present invention is a sterile covering for use in combination with an endoscope and a camera which has a lens-to-endoscope coupling. The coupling temporarily couples the endoscope to the camera. The covering comprises a body portion for covering the camera and an end portion for enclosing the coupling and for defining a barrier by interposition between the camera and endoscope. The end portion includes a first means for providing a clear optical path between the camera and endoscope and includes a second means for registering the first means within the coupling in order to align it with the optical path between the camera and endoscope. By this combination of elements, the endoscope may be successively coupled and uncoupled from the coupling without contamination of the endoscope by the camera, and without destruction of the sterility of the covering for the camera.

In one embodiment, the second means is a generally circular, resilient coupling element which resiliently and circumferentially engages the lens-to-endoscope coupling. The element is also coupled to the end portion of the covering, thereby circumscribing a central portion of the end portion. This central portion includes the first means which provides a clear optical path between the camera and the endoscope.

In a second embodiment, the lens-to-endoscope coupling comprises a cylindrical C-mount and the second means includes a first disc having a circumferential edge portion adapted to complementarily fit within the C-mount and to further provide a clear optical path at a preselected area on the disc.

In a third embodiment, the lens-to-endoscope coupling includes a C-mount which has a cylindrical cavity. The second means includes a cylindrical cup which is adapted to fit into the cavity. A ring overlies the cup. The end portion of the covering is secured to the cup and is disposed between the cup and the ring. The cup has a central portion registered with the optical path between the endoscope and camera. The central portion is optically clear and substantially fluid impermeable.

These and other embodiments are best understood by viewing the following Figures, wherein like elements are referenced by like numerals.

BRIEF DESCRIPTION OF THE DRAWINGS

FIG. 1 is a simplified perspective view of a camera and endoscope without the present invention.

FIG. 2 is the view of FIG. 1 with the present invention in place.

FIG. 3 is an end view in enlarged scale taken through section 3—3 of FIG. 1.

FIG. 4 is an end view in enlarged scale taken through section 4—4 of FIG. 2.

FIG. 5 is a sectional view of a first embodiment taken through section 5—5 of FIG. 4.

FIG. 6 is a sectional view of a second embodiment in enlarged scale of the endoscope to C-mount coupling.

FIG. 7 is a sectional view of a third embodiment showing in enlarged scale the endoscope to C-mount coupling.

FIG. 8 is a partial sectional view of the end portion of a fourth embodiment of the sterile covering.

DETAILED DESCRIPTION OF THE PREFERRED EMBODIMENTS

The present invention is a sterile covering for use in combination with a camera and an endoscope which is coupled to the camera by means of a C-mount. The covering of the present invention allows the endoscope to be coupled and uncoupled from the camera without contamination and further preserves the quality of the optical path between the endoscope and the camera.

FIG. 1 illustrates the environment in which the present invention is used. Camera 10 is shown in simplifed perspective view as being coupled to an endoscope 12 by means of a coupling 14. As shown in FIGS. 1 and 3, coupling 14 is a conventional C-mount coupling, and includes a plurality of manually actuated rollers 16. These are pressed tightly against the flared end 18 of endoscope 12, as seen in FIGS. 5–7, to provide a quick release mechanism for coupling endoscope 12 to camera 10.

Rollers 16 are actuated by manually rotating ring 20 of coupling 14. The details of the mechanism of coupling 14 by which rollers 16 are advanced against flared end 18 to lock the endoscope into place are well known and are therefore omitted for brevity.

FIG. 3 illustrates central clear optical portion 22 of endoscope 12. Central portion 22 defines the optical field as seen by camera 10, which field is transmitted to the receiving lens 26 of camera 10 by endoscope 12. The clarity of this optical field must not be degraded, and for this reason, the prior art pratice has been to dispose endoscope 12 within coupling 14 in such a manner that end 24 of endoscope 12, shown in FIGS. 5-7, is placed in immediate contact with coupling 14 or receiving lens 26 of camera 10.

FIG. 2 illustrates covering 28 of the present invention placed over camera 10. One end 30 of covering 28 is tied in a conventional manner around camera 10 or its transmission cable 32 to provide a tight, sterile barrier. This end remains sealed at all times during the operation. The opposing end 34 of covering 28 is associated with the coupling 14 in the manner described below. In the embodiment illustrated in FIG. 2, end portion 34 of covering 28 is disposed within a cavity defined within coupling 14.

As better shown in FIGS. 4-7, end portion 34 is disposed within coupling 14 and underneath flared end 18 of endoscope 12. Rollers 16 are covered by end portion 34 and when actuated clamp end 18 and press end portion 34 tightly against flared end 18 of endoscope 12. End portion 34 is positioned on coupling 14 and registered with respect to the endoscope-to-camera optical path by means of a resilient, elastomeric ring 36 which is coupled or fixed to that portion of covering 28 which overlies the circumferential portions of coupling 14, and in particular the ring 20.

Referring now to FIGS. 2, 4 and 5, elastomeric ring 36 is adhered to covering 28 and circumscribes end portion 34, which fits into cavity 15 and against the annular base of the cavity 15 defined by coupling 14. End portion 34 has an aperture 38 defined therein which is registered by means of ring 36 with the endoscope-to-camera optical path. Therefore, ring 36 not only serves to secure end portion 34 of covering 28 in place, but also serves to register aperture 38. Ring 20 is rotated to actuate rollers 16, thereby clamping endoscope 12 to coupling 14. Elastomeric ring 36, which was disposed to the left of ring 20 as viewed in FIG. 5 when ring 20 was rotated, is then drawn back over ring 20 and resiliently stretched over ring 20 and coupling 14, thereby tightly drawing up end portion 34 of covering 28.

Although the embodiment illustrated in FIGS. 2-5 provides a means for registering aperture 38 with the endoscope-to-camera optical path, the opening of aperture 38 in end portion 34 of covering 28 gives rise to the slight possibility of contamination of end 24 of endoscope 12 from camera 10 or coupling 14. The embodiments of FIGS. 6, 7 and 8 avoid even this slight possibility.

More particularly, in the second embodiment illustrated in FIG. 6, end portion 34 of covering 28 is continuous and has no apertures or perforations. An optically clear base or portion 40 is disposed in and registered with the endoscope-to-camera optical path by means of a first disc 42 disposed within cavity 15 defined by coupling 14. Disc 42 has a central aperture 44 defined therein which is registered with the optical path and across which optically clear portion 40 of end portion 34 is disposed.

Although it is possible that only a single disc 42 may be disposed within cavity 15 of coupling 14, it is also within the scope of the present invention that a second disc 46 could be disposed therein. Second disc 46 is substantially similar to first disc 42 and has a central aperture 48 defined therein. End portion 34 is in this case sandwiched between discs 46 and 42, thereby reducing the likelihood and possibility that any wrinkles will form in clear portion 40 which would interfere with the clarity of the optical image.

Portion 40 may be a separate end section or thin film disposed between discs 42 and 46 or at least on disc 42. For example, end portion 34 may have a large aperture formed therein with a diameter slightly smaller than the internal diameter of cavity 15. A thin circular film is then disposed on disc 42 or between discs 46 and 42 to specially provide a clear optical path. In this manner, a thicker, tougher and, if desired, opaque material may be used for covering 28 while a thinner, more delicate and specially formed optical film could be used for central portion 40 of end portion 34. Such a thin film could include a thin layer of glass, a filter element, or any well known optically clear, plastic film.

FIG. 7 illustrates a third embodiment wherein covering 28 has its end portion 34 coupled to a preformed element or cup 50 which is preformed to particularly conform to the internal dimensions of cavity 15 and the end of endoscope 12. Thus, covering 28 may be formed of a tough, flexible, relatively opaque material, while cup 50 may be formed of a rigid or semirigid, optically clear material. Cup 50 has no apertures or perforations defined therein and provides a complete barrier between end 24 of endoscope 12 and camera 10 or coupling 14.

As seen in FIG. 8, it is entirely within the scope of the present invention that cup 50 may also define an aperture 41 in central portion 40 and thin film 40a disposed thereover in a manner similar to that described in connection with FIG. 6, or covering 28 may be extended and disposed in cavity 15 to provide a barrier across such an aperture in cup 50.

End portion 34 of covering 28 may be coupled to cup 50 by any means well known to the art and, in particular, may be bonded and coupled thereto with the aid of a ring member 52 disposed over the peripheral edge of end portion 34 of covering 28 and end portion 54 of cup 50.

From the foregoing, it will be seen that the embodiments of FIGS. 6 and 7 provide a fluid impermeable barrier and a sterile seal between endoscope 12 and camera 10 or coupling 14. In addition, each of the illustrated embodiments has a means for registering an optically clear aperture or member with respect to the endoscope-to-camera optical path.

Various alterations and modifications may be made to the present invention without departing from its spirit and scope. For example, although the embodiments of FIGS. 6 and 7 have shown elements which are fixed or secured to covering 28, it is also comprehended that the fixation of end portion 34 either to discs 42 and 46 or cup 50 may be temporarily accommodated by conventional means, such as by providing a snap interlocking circular lip and groove in discs 46 and 42, respectively, or in ring member 52 and end portion 54 of cup 50, respectively. In this manner, various types of cups or thin films or filter may be coupled to the same covering 28 through a snap fitting, as devised.

The present embodiments have been shown only for the purposes of illustration, and should not be taken as limiting or restricting the scope of the present invention other than as set forth in the following claims.

I claim:

1. A sterile covering for use in combination with an endoscope and a camera having a lens-to-endoscope coupling characterized by a cavity adapted to receive one end of said endoscope adjacent the base of said cavity, said coupling being operative to temporarily couple said endoscope within said cavity, said covering comprising:

a flexible body portion for covering said camera; and
an end portion attached to said body portion and made of material which is rigid relative to the flexible material of said body portion for repeated insertion into and withdrawal from said cavity without losing its shape, said end portion including an end portion base for location adjacent the base of said cavity, said end portion base having an optically clear central section for providing a clear optical path between said camera and said endoscope, said end portion base further including a layer of flexible and optically clear material which is thin relative to the material of said end portion, said layer being attached to said end portion base in registry with said central section for alignment with the optical path between said camera and endoscope whereby said endoscope may be successively coupled and decoupled from said coupling without contamination of said endoscope by said camera.

2. The covering of claim 1 wherein said lens-to-endoscope coupling is a "C"-mount, said cavity is cylindrical, and said end portion comprises a cylindrical cup adapted to fit in said cavity.

3. An improvement in a sterile covering for an endoscope having a flared end collar, and for a camera having a quick-release coupling for engaging and retaining said end collar, and wherein said covering is characterized by a body portion covering said camera and an end portion covering at least part of said quick-release coupling, said improvement comprising:

an optically clear member made of thin and flexible material for providing an antiseptic barrier between said end collar and said quick-release coupling; and
cup means incorporated in said end portion made of material which is tough and rigid relative to the material of said optically clear member for repeated insertion into and withdrawal from within said quick-release coupling, and mounting said optically clear member for optical alignment with said camera, whereby contamination between said endoscope and said quick-release coupling is substantially prevented.

4. The improvement of claim 3 wherein said coupling comprises a "C"-mount having a cylindrical cavity and said cup means comprises a cylindrical cup disposable within said cavity, said cup having a base mounting said optically clear member, said optically clear member being attached adjacent its periphery to said end portion whereby said end portion extends into said cavity between said end collar and said coupling.

5. The improvement of claim 4 wherein said end portion is coupled to said cup means exteriorly of said "C"-mount.

6. The improvement of claim 3 wherein said optically clear member comprises an aperture in said cup means.

7. A method for providing a sterile covering between the coupling of a camera and one end of an endoscope during a surgical procedure, said method comprising the steps of:

disposing over said camera a sterile covering having an optically clear member;
extending said covering over and into said coupling with said member in the optical path between said one end of said endoscope and said camera; attaching said covering to a centrally apertured preformed element with said optically clear member in alignment with the aperture in said preformed element, and disposing said preformed element within the interior of said coupling in engagement therewith, said preformed element being selected of material which is thick relative to the material of said optically clear member whereby said preformed element can be repeatedly inserted into and withdrawn from said interior of said coupling without losing its shape, thereby being adapted to maintain registry of said optically clear member with said optical path; and
disposing said one end of said endoscope into said couping adjacent said covering whereby said covering defines a barrier between said endoscope and camera to substantially prevent contamination therebetween.

8. The method claim of 7 wherein said preformed element is cup shaped.

* * * * *